(12) United States Patent
Xu et al.

(10) Patent No.: US 11,116,592 B2
(45) Date of Patent: Sep. 14, 2021

(54) FLEXIBLE SURGICAL INSTRUMENT SYSTEM BASED ON CONTINUOUS BODY STRUCTURE

(71) Applicant: BEIJING SURGERII TECHNOLOGY CO., LTD., Beijing (CN)

(72) Inventors: Kai Xu, Beijing (CN); Zhengchen Dai, Beijing (CN); Shu'an Zhang, Beijing (CN); Jiangran Zhao, Beijing (CN); Zhixiong Yang, Beijing (CN); Yuyang Chen, Beijing (CN); Wei Wei, Beijing (CN)

(73) Assignee: BEIJING SURGERII TECHNOLOGY CO., LTD., Beijing (CN)

( * ) Notice: Subject to any disclaimer, the term of this patent is extended or adjusted under 35 U.S.C. 154(b) by 247 days.

(21) Appl. No.: 16/329,730

(22) PCT Filed: Aug. 30, 2017

(86) PCT No.: PCT/CN2017/099755
§ 371 (c)(1),
(2) Date: Feb. 28, 2019

(87) PCT Pub. No.: WO2018/041159
PCT Pub. Date: Mar. 8, 2018

(65) Prior Publication Data
US 2019/0192241 A1    Jun. 27, 2019

(30) Foreign Application Priority Data

Aug. 31, 2016    (CN) .......................... 201610798125.2

(51) Int. Cl.
*A61B 34/30* (2016.01)
*A61B 17/00* (2006.01)
(Continued)

(52) U.S. Cl.
CPC ............ *A61B 34/30* (2016.02); *A61B 1/0055* (2013.01); *A61B 17/00* (2013.01);
(Continued)

(58) Field of Classification Search
CPC ........ A61B 2034/305; A61B 2034/306; A61B 34/71; A61B 17/00234;
(Continued)

(56) References Cited

U.S. PATENT DOCUMENTS

| 2010/0170519 A1* | 7/2010 | Romo | A61B 34/30 |
| | | | 128/852 |
| 2013/0090763 A1* | 4/2013 | Simaan | A61B 5/11 |
| | | | 700/258 |

(Continued)

FOREIGN PATENT DOCUMENTS

| CN | 101653353 A | 2/2010 |
| CN | 103025225 A | 4/2013 |

(Continued)

OTHER PUBLICATIONS

State Intellectual Property Office of the People's Republic of China, First Search Issued in Application No. 201610798125.2, dated May 27, 2018, 4 pages.

(Continued)

*Primary Examiner* — Katherine H Schwiker
(74) *Attorney, Agent, or Firm* — McCoy Russell LLP

(57) ABSTRACT

Disclosed is a flexible surgical instrument system comprising a flexible surgical instrument and a driving unit. The flexible surgical instrument comprises a flexible continuous body structure composed of a distal structural body, a proximal structural body. The driving unit comprises a motor part, a motion conversion part and a plurality of linear motion mechanisms. The motor part comprises a motor fixing plate and a first motor. The motion conversion part
(Continued)

comprises a plurality of first transmission chains, each of the first transmission chains converts rotary output of the first motor into a linear motion of two first output rods and the linear motion each of the two first output rods is transferred to an input end of each of the linear motion mechanisms through a sterile barrier, an output end of each of the linear motion mechanisms is connected to one end of one driving backbone.

13 Claims, 14 Drawing Sheets

(51) Int. Cl.
*A61B 1/005* (2006.01)
*A61B 1/00* (2006.01)

(52) U.S. Cl.
CPC .... *A61B 17/00234* (2013.01); *A61B 1/00147* (2013.01); *A61B 2017/00323* (2013.01); *A61B 2017/00398* (2013.01); *A61B 2034/301* (2016.02); *A61B 2034/305* (2016.02)

(58) Field of Classification Search
CPC ........... A61B 2017/00314; A61B 2017/00323; A61B 34/30–37; A61B 2034/301–306; A61B 17/29–295; A61B 2017/2901–2948; A61B 2017/00238–00362; A61B 2017/00398; A61B 1/0055; B25J 8/06; B25J 9/104; B25J 918/06
See application file for complete search history.

(56) References Cited

U.S. PATENT DOCUMENTS

| | | | |
|---|---|---|---|
| 2014/0330432 A1 | 11/2014 | Simaan et al. | |
| 2015/0223832 A1* | 8/2015 | Swaney | A61B 34/10 606/130 |
| 2015/0352728 A1* | 12/2015 | Wang | A61B 1/00 74/490.04 |

FOREIGN PATENT DOCUMENTS

| | | |
|---|---|---|
| CN | 103085083 A | 5/2013 |
| CN | 103707322 A | 4/2014 |
| CN | 103948435 A | 7/2014 |
| CN | 103707322 B | 4/2016 |
| CN | 105751210 A | 7/2016 |
| CN | 105856213 A | 8/2016 |
| CN | 106361433 A | 2/2017 |
| EP | 2777595 A2 | 9/2014 |
| WO | 2009094670 A1 | 7/2009 |
| WO | 2012015816 A1 | 2/2012 |
| WO | 2013158978 A1 | 10/2013 |
| WO | 2015175200 A1 | 11/2015 |

OTHER PUBLICATIONS

European Patent Office, Supplementary European Search Report Issued in Application No. 17845461.7, dated Mar. 26, 2020, Germany, 3 pages.

ISA State Intellectual Property Office of the People's Republic of China, International Search Report Issued in Application No. PCT/CN2017/099755, dated Dec. 4, 2017, WIPO, 6 pages.

* cited by examiner

US 11,116,592 B2

FLEXIBLE SURGICAL INSTRUMENT SYSTEM BASED ON CONTINUOUS BODY STRUCTURE

CROSS REFERENCE TO RELATED APPLICATIONS

The present patent application is a U.S. National Phase of Chinese International Application No. PCT/CN2017/099755, entitled "FLEXIBLE SURGICAL INSTRUMENT SYSTEM BASED ON CONTINUOUS BODY STRUCTURE", and filed on Aug. 30, 2017. Chinese International Application No. PCT/CN2017/099755 claims priority to Chinese Patent Application No. 201610798125.2 filed on Aug. 31, 2016. The entire contents of each of the above-identified applications are incorporated herein by reference for all purposes.

TECHNICAL FIELD

The present invention relates to a flexible surgical instrument system based on a continuous body structure, belonging to the field of medical instruments.

BACKGROUND ART

Multi-port laparoscopic minimally invasive surgery has occupied an important position in surgery because of it having small wound and rapid postoperative recovery. The existing da Vinci surgical robot of the Intuitive Surgical, Inc. assists doctors in implementing the multi-port laparoscopic minimally invasive surgery and has achieved great commercial success.

For the minimally invasive surgery, after the multi-port laparoscopic surgery, single-port laparoscopic surgery and natural orifice transluminal non-invasive surgery have been further developed and have less trauma to the patient and higher postoperative outcomes. However, in the single-port laparoscopic surgery and the natural orifice transluminal non-invasive surgery, all surgical instruments including a visual illumination module and a surgical manipulator have access to the surgical site through a single channel, which is extremely stringent for the preparation of the surgical instruments. A distal structure of the existing surgical instrument is mainly of multiple rods articulated in series, and is driven by a pulling force from a steel wire rope, so that the surgical instrument can turn at an articulated joint. Since the steel wire rope has to be continuously tensioned by a pulley, this driving method can hardly lead to further miniaturization of the surgical instrument, and also further improvement of the moving performance of the instrument.

Although the Intuitive Surgical, Inc. recently introduces a da Vinci Single-Site surgical robot, in which the original rigid surgical instrument is modified into a semi-rigid surgical instrument and a pre-bent sleeve is additionally provided so as to improve the moving performance of the surgical instrument to a certain extent, it is still impossible to fundamentally solve the problems faced by the traditional microsurgical instruments.

SUMMARY OF THE INVENTION

Aiming at the above problems, an object of the present invention is to provide a flexible surgical instrument system based on a continuous body structure that can be better applied to a robot system which passes through a natural orifice of human body or a single surgical incision and performs an operation.

In order to achieve the above object, the following technical solutions are used in the present invention: a flexible surgical instrument system based on a continuous body structure, the flexible surgical instrument system comprising a flexible surgical instrument and a driving unit; wherein the flexible surgical instrument comprises a flexible continuous body structure composed of a distal structural body, a proximal structural body and a middle connecting body; the distal structural body comprises at least one distal structural segment comprising a distal spacing disk, a distal fixing disk and structural backbones; the proximal structural body comprises a proximal structural segment comprising a proximal spacing disk, a proximal fixing disk and structural backbones; the middle connecting body comprises two channel fixing plates and a structural backbone guide channel provided between the two channel fixing plates; the structural backbones of the distal structural segment are securely connected, in one-to-one correspondence, to or are the same as the structural backbones of the proximal structural segment, one end of each of the structural backbones is securely connected to the proximal fixing disk, passing through the proximal spacing disk, the structural backbone guide channel, and the distal spacing disk in sequence, and the other end of the structural backbone is securely connected to the distal fixing disk; and the driving unit comprises a motor part, a motion conversion part and a plurality of linear motion mechanisms, wherein a sterile barrier is provided between the motion conversion part and the linear motion mechanism; and the motor part comprises a first fixing plate and a first motor securely connected to the first fixing plate, the motion conversion part comprises a plurality of transmission chains, each of the transmission chains converts a rotary output of the first motor into a linear motion of two output rods, the linear motion of the output rods is transferred to an input end of the linear motion mechanism through the sterile barrier, an output end of the linear motion mechanism is securely connected to one end of one driving backbone passing through the proximal spacing disk, and the other end is securely connected to the proximal fixing disk.

Preferably, the number of proximal structural bodies is equal to the number of distal structural segments.

In one embodiment, the linear motion mechanism can comprise a shaft securely connected between the two channel fixing plates and a slider slidably connected to the shaft, the slider serves as the output end of the linear motion mechanism and is securely connected to the driving backbone, the slider is also securely connected to one end of a push-pull rod, and the other end of the push-pull rod passes through the channel fixing plates and is connected to the output rod through the sterile barrier.

In one embodiment, the motion conversion part can further comprise a second fixing plate, a third fixing plate and a fourth fixing plate which are provided in front of the first fixing plate; each of the transmission chains comprises a first threaded rod and a second threaded rod which are spaced apart and rotatably supported between the third fixing plate and the fourth fixing plate, and the rear end of the first threaded rod passes through the third fixing plate and the second fixing plate in sequence and is connected to an output shaft of the first motor via a coupling; a first gear is securely connected to the first threaded rod between the second fixing plate and the third fixing plate, the first gear is in transmission connection with a second gear via an idle gear, and the second gear is securely connected to the second threaded rod; a first nut and a second nut are respectively connected, in a matching manner, to the first threaded rod and the second threaded rod between the third fixing plate and the fourth fixing plate; and the two output rods are respectively securely connected to the first nut and the second nut, and front ends of the output rods pass through the fourth fixing plate.

In one embodiment, the sterile barrier can comprise a first isolation plate, a second isolation plate, a plurality of sleeves securely connected between the first isolation plate and the second isolation plate, and base guide rods having the same number as the sleeves; one end of each of the base guide rods is connected to the front end of one of the output rods via a locking mechanism, and the other end of the base guide rod extends into the sleeve and is connected to the rear end of one push-pull rod via a quick-locking mechanism; and a sterile membrane for isolating a sterilizable part from an unsterilized part of the flexible surgical instrument system is securely connected to the first isolation plate.

In one embodiment, the quick-locking mechanism can comprise an engagement block, an engagement groove matching the engagement block is provided at the rear end of the push-pull rod, and two articulation points are provided at the rear part of the engagement block, with one of the articulation points being articulated with the base guide rod, the other articulation point being connected to one end of a rocking bar via a connecting rod, and the other end of the rocking bar being articulated with the base guide rod; the sleeve is provided with a first groove for the engagement block, the connecting rod and the rocking bar to rotate; and the front side of the second isolation plate is connected with a return spring, and a return baffle ring is securely connected to the front end of the return spring; wherein when the return spring is in a loosened state, the return baffle ring is attached to the first groove of the sleeve and abuts against a connecting point of the connecting rod and the rocking bar.

In one embodiment, the rear side of the first isolation plate can be provided with a switch baffle ring which is slidably connected to the respective sleeve, the switch baffle ring is sheathed over the respective sleeves via through holes, a protrusion feature is provided in the respective through hole of the switch baffle ring, a second groove is provided on the side of the sleeve opposite to the first groove, and the connecting rod is a U-shaped connecting rod with one end being close to the second groove; and when the switch baffle ring moves backward along the respective sleeve, the respective protrusion feature slides along the second groove and touches the end of the U-shaped connecting rod, enabling the U-shaped connecting rod to rotate.

In one embodiment, the locking mechanism can comprise a locking head with a threaded through hole that is securely connected to the base guide rod, a locking screw is connected, in a matching manner, into the threaded through hole, and when being screwed into the threaded through hole, the locking screw tightly abuts against the output rod.

In one embodiment, a surgical end effector can be provided in the front end of the distal structural body, a actuation wire of the surgical end effector passes through the distal structural body, the other end of the distal structural body is connected to a surgical end effector driving mechanism on the channel fixing plate, the surgical end effector driving mechanism comprises a base securely connected to the channel fixing plate, a connecting rod is rotatably provided on the base, one end of the connecting rod is connected with a first slider which is securely connected to a second push-pull rod, and the rear end of the second push-pull rod passes through the channel fixing plate and extends backward; the other end of the connecting rod is connected with a second slider which is slidably connected into a sliding groove securely connected to the channel fixing plate, and the second slider is securely connected to the actuation wire; a second motor is securely connected to the first fixing plate, and the motion conversion part further comprises a second transmission chain which converts a rotary output of the second motor into a linear motion of a second output rod; and the linear motion of the second output rod is transferred to the second push-pull rod via the sterile barrier.

In one embodiment, the motion conversion part can further comprise a second fixing plate, a third fixing plate and a fourth fixing plate which are provided in front of the first fixing plate; and the second transmission chain comprises a third threaded rod, the rear end of the third threaded rod is connected to the second motor via a coupling between the first fixing plate and the second fixing plate, both the third fixing plate and the fourth fixing plate rotatably support the third threaded rod, a third nut is connected, in a matching manner, to the third threaded rod between the third fixing plate and the fourth fixing plate, and the third nut is securely connected to the second output rod.

In one embodiment, the flexible surgical instrument system can further comprise a shell, the first fixing plate is rotatably connected to the shell, and an inner ring gear is securely connected to an inner wall of the shell; and a third motor is securely connected to the first fixing plate, an output shaft of the third motor is connected to a shaft via a coupling, and the front end of the shaft is securely connected to a gear in transmission connection with another gear via an idle gear, the another gear meshing with the inner ring gear.

In one embodiment, the flexible surgical instrument system can further comprise a shell and a linear module, the linear module comprises a support body, a fourth motor securely connected to the support body, and a linear feed mechanism securely connected to an output shaft of the fourth motor, wherein an output end of the linear feed mechanism is securely connected to the shell, and the fourth motor drives the shell by means of the linear feed mechanism, to drive the driving unit, the sterile barrier and the flexible surgical instrument to perform a linear motion.

In one embodiment, the linear feed mechanism can comprise a lead screw rotatably connected to the support body, the lead screw is sheathed with a third slider which is threadedly fitted with the lead screw, a linear sliding groove is provided on the support body, and the third slider is slidably provided in the linear sliding groove; and the output shaft of the fourth motor is securely connected to the lead screw via a coupling.

In one embodiment, the screw direction of the first threaded rod is different from that of the second threaded rod, and the screw pitch of the first threaded rod is the same as that of the second threaded rod.

The present invention has the following advantages due to utilizing the above technical solutions: 1. In the present invention, a flexible continuous body structure comprising a proximal structural body, a middle connecting body and a distal structural body is used as the main body, and cooperates with a driving unit, wherein the distal structural body is linked to the proximal structural body via the middle connecting body, the driving unit is linked to the proximal structural body, and when the driving unit drives the proximal structural body to turn in any direction, the distal structural body correspondingly turns in the opposite direction, so as to implement the turning motion in any direction of a flexible surgical arm formed of the distal structural body and an envelope. 2. The driving unit in the present invention comprises linear motion mechanisms, a motor part and a motion conversion part, wherein a push-pull rod of the linear motion mechanism is connected to the proximal structural body via a driving backbone, a transmission chain in the motion conversion part can convert an output of one motor in the motor part into a cooperative linear motion of two output rods, and the output rods are connected to the push-pull rod of the linear motion mechanism via a sterile barrier, thereby effectively isolating an unsterilized part from a sterilized part of the system, and ensuring the practicability of clinical surgery. 3. The sterile barrier in the present invention comprises base guide rods, one end of each of the base guide rods is connected to the output rod of the transmission chain via a locking mechanism, and the other end of the base guide rod is connected to the push-pull rod of the linear motion mechanism via a quick-locking mechanism, thus enhancing the modularity and flexibility of the whole system. 4. In the present invention, a surgical end effector is provided in the front end of the distal structural body, a actuation wire of the surgical end effector passes through the distal structural body, and the other end is connected to a surgical end effector driving mechanism in the middle connecting body; and the motor part is provided with a motor for driving the push and pull of the actuation wire, and the output of the motor passes through the sterile barrier via another transmission chain and reaches the surgical end effector driving mechanism, thereby realizing motion control over the surgical end effector. 5. The present invention is further provided with a shell, the driving unit and the shell are connected in a rotatable manner, an inner ring gear is securely provided on an inner wall of the shell, the motor part is provided with a motor for driving the part except for the shell and the inner ring gear, and the gear securely connected to an output shaft of the motor is connected to another gear via an idle gear, the another gear meshing with the ring gear. Therefore, the motor can be used to drive the part except for the shell and the inner ring gear to rotate as a whole, thereby adjusting the roll angle of the surgical end effector. 6. The present invention is further provided with a linear module, which is connected to the shell and can drive the shell to perform a linear motion, and therefore, the flexible surgical arm also has a linear feed degree of freedom.

The present invention can be applied to the single-port endoscopic surgery, and can also be applied to the natural orifice transluminal non-invasive surgery.

DETAILED DESCRIPTION OF EMBODIMENTS

The present invention is described in detail below in conjunction with the accompanying drawings and embodiments.

Figure 1:
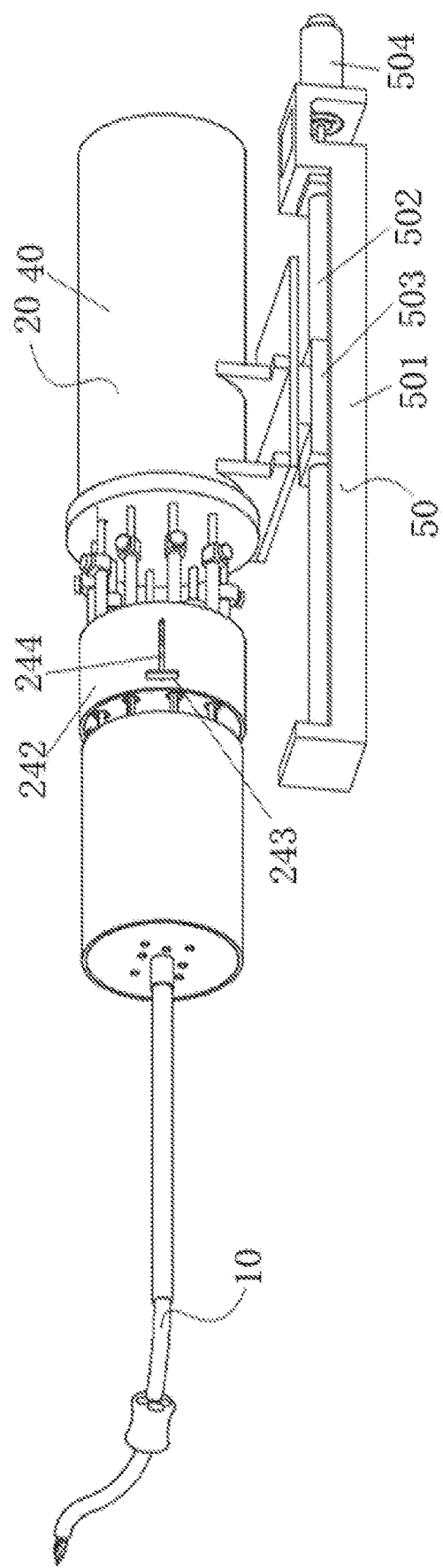
FIG. 1 is an overall structural schematic diagram according to the present invention.
Figure 2:
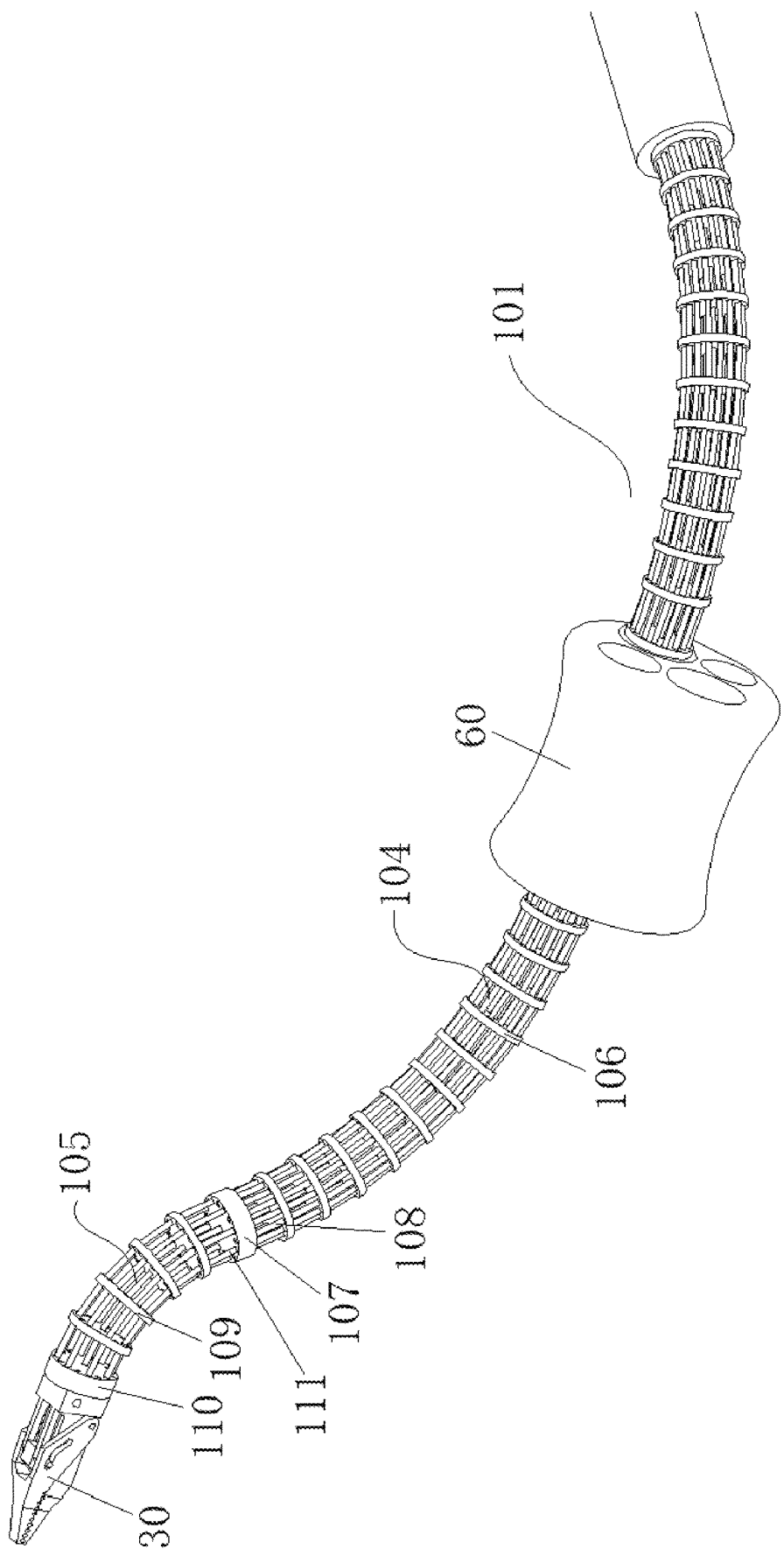
FIG. 2 is a structural schematic diagram of a distal structural body according to the present invention.
Figure 3:
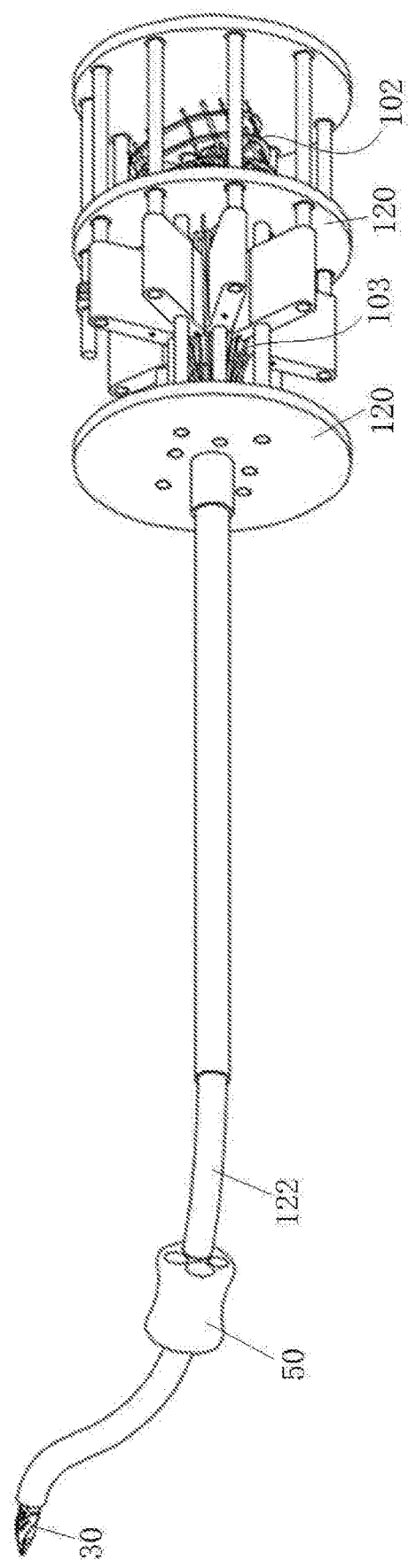
FIG. 3 is a structural schematic diagram of a flexible continuous body structure according to the present invention where an envelope is sheathed outside the distal structural body.
Figure 5:
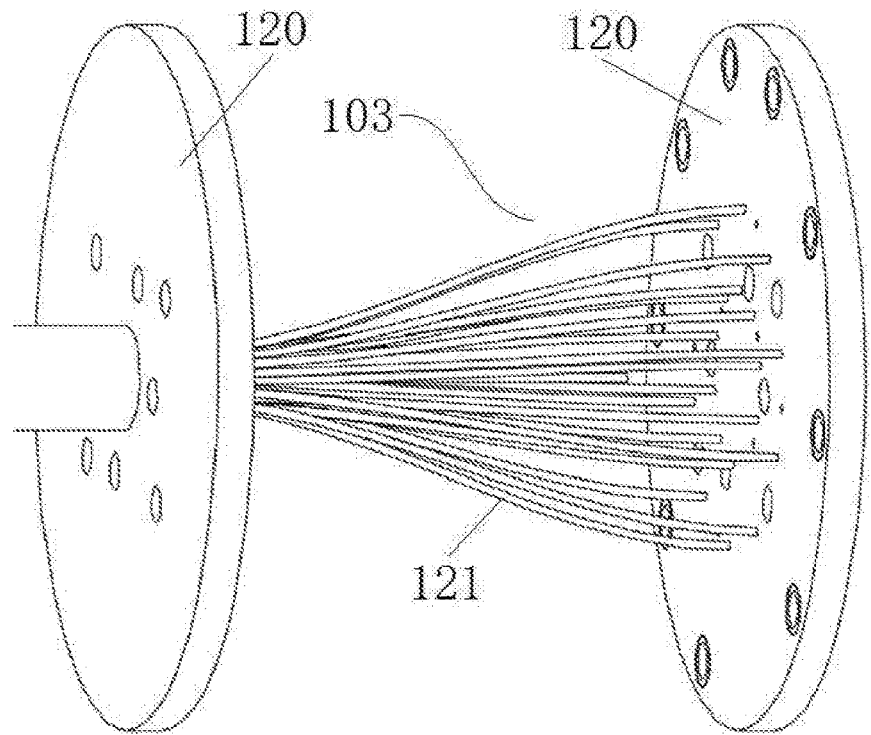
FIG. 5 is a structural schematic diagram of a middle connecting body according to the present invention.

As shown in FIG. 1, the present invention comprises a flexible surgical instrument 10 and a driving unit 20. The flexible surgical instrument 10 comprises a flexible continuous body structure composed of a distal structural body 101 (as shown in FIG. 2), a proximal structural body 102 (as shown in FIG. 3) and a middle connecting body 103 (as shown in FIG. 5); wherein the distal structural body 101 is linked to the proximal structural body 102 via the middle connecting body 103; The driving unit 20 is linked to the proximal structural body 102, and when the driving unit 20 drives the proximal structural body 102 to turn in any direction, the distal structural body 101 correspondingly turns in the opposite direction.

As shown in FIG. 2, the distal structural body 101 comprises two distal structural segments 104, 105, wherein the first distal structural segment 104 comprises first distal spacing disks 106, a first distal fixing disk 107 and first segment structural backbones 108. The second distal structural segment 105 comprises second distal spacing disks 109, a second distal fixing disk 110 and second segment structural backbones 111. Wherein the first distal spacing disks 106 and the second distal spacing disks 109 are respectively distributed at intervals in the first distal structural segment 104 and the second distal structural segment 105, in order to prevent the first segment structural backbones 108 and the second segment structural backbones 111 from being destabilized when being pushed.

Figure 4:
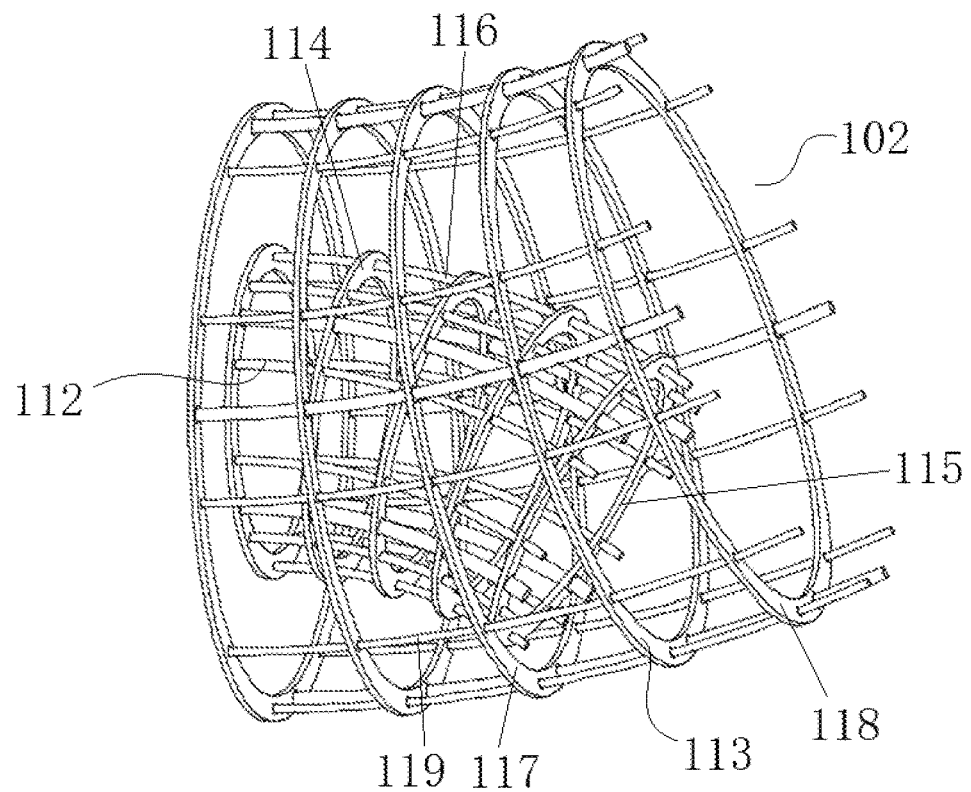
FIG. 4 is a structural schematic diagram of a proximal structural body according to the present invention.

As shown in FIGS. 3 and 4, the proximal structural body 102 comprises two proximal structural segments 112, 113, wherein the first distal structural segment 112 comprises first proximal spacing disks 114, a first proximal fixing disk 115 and first segment structural backbones 116; and the second proximal structural segment 113 comprises second proximal spacing disks 117, a second proximal fixing disk 118, and second segment structural backbones 119; wherein the first proximal spacing disks 114 and the second proximal spacing disks 117 are respectively distributed at intervals in the first proximal structural segment 112 and the second proximal structural segment 113, in order to prevent the first segment structural backbones 116 and the second segment structural backbones 119 from being destabilized when being pushed. The first segment structural backbones 116 in the first proximal structural segment 112 are securely connected, in one-to-one correspondence, to or are the same as the first segment structural backbones 108 in the first distal structural segment 104; and the second segment structural backbones 119 in the second proximal structural segment 113 are securely connected, in one-to-one correspondence, to or are the same as the second segment structural backbones 111 of the second distal structural segment 105. For each of the proximal structural segments 112, 113 and each of the distal structural segments 104, 105, the number of structural backbones is three or more.

As shown in FIG. 5, the middle connecting body 103 comprises two channel fixing plates 120 and a structural backbone guide channel 121 fixedly connected between the two channel fixing plates 120. One end of the first segment structural backbone 116 (108) is securely connected to the first proximal fixing disk 115, and the other end passes through the first proximal spacing disks 114, the structural backbone guide channel 121 and the first distal spacing disks 106 in sequence and is then securely connected to the first distal fixing disk 107. One end of the second segment structural backbone 119 (111) is securely connected to the second proximal fixing disk 118, and the other end passes through the second proximal spacing disks 117, the structural backbone guide channel 121, the first distal structural segment 104 and the second distal spacing disks 109 in sequence and is then securely connected to the second distal fixing disk 110. The structural backbone guide channel 121 functions to maintain the shape of the structural backbone under a pushing or pulling force.

The number of the distal structural segments comprised in the distal structural body 101 and the number of the proximal structural segments comprised in the proximal structural body 102 may also be one or more than two, but the number of the proximal structural segments must be consistent with the number of the distal structural segments. In addition, when the number of the distal structural segments comprised in the distal structural body 101 is two or more, the distal structural segments are connected in series, that is, the second segment structural backbone passes through the first distal fixing disk and the first distal spacing disks (and can also pass through the first segment structural backbone if the first segment structural backbone is of a tubular structure); When the number of the proximal structural segments comprised in the proximal structural body 102 is two or more, series connection, independent arrangement or nested arrangement (as shown in FIG. 4), etc. may be applied between the structural segments.

Figure 6:
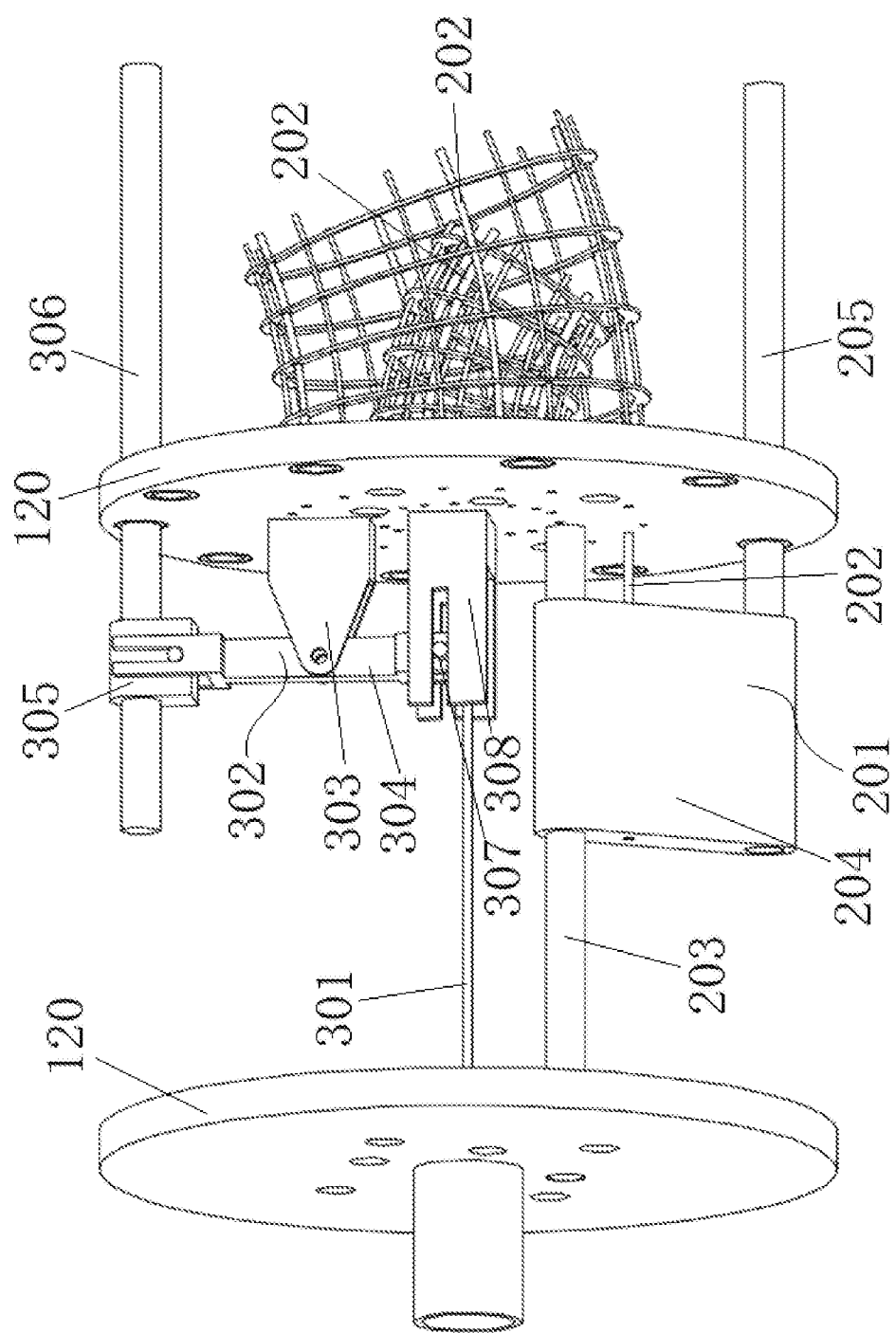
FIG. 6 is a structural schematic diagram of a linear motion mechanism and a surgical end effector driving mechanism according to the present invention.

The driving unit 20 comprises a plurality of linear motion mechanisms 201 (as shown in FIGS. 3 and 6) provided between the two channel fixing plates 120, each of the linear motion mechanisms 201 comprises one push-pull rod 205 and one slider 204 securely connected to the push-pull rod 205, the slider 204 is securely connected to one end of one driving backbone 202, the other end of the driving backbone 202 passes through the first proximal spacing disks 114 and is then securely connected to the first proximal fixing disk 115 or passes through the second proximal spacing disks 117 and is then securely connected to second proximal fixing disk 118. In this embodiment, eight driving backbones 202 are provided, four of which are connected to the first proximal fixing disk 115, and the other four ones are connected to the second proximal fixing disk 118. By means of the linear motion mechanisms 201 cooperatively pushing and pulling the driving backbones 202 connected to the first proximal structural segment 112, two degrees of freedom for the first proximal structural segment 112 to turn in any direction can be achieved; and when the first proximal structural segment 112 turns in a certain direction, the first distal structural segment 104 will turn in the opposite direction in a certain proportional relationship (determined by the distribution radius of the first segment structural backbone 116 and the first segment structural backbone 108 together). Similarly, by means of the linear motion mechanisms 201 cooperatively pushing and pulling the driving backbones 202 connected to the second proximal structural segment 113, two degrees of freedom for the second proximal structural segment 113 to turn in any direction can be achieved; and when the second proximal structural segment 113 turns in a certain direction, the second distal structural segment 105 will turn in the opposite direction in a certain proportional relationship (determined by the distribution radius of the second segment structural backbone 119 and the second segment structural backbone 111 together).

As shown in FIG. 6, the linear motion mechanism 201 further comprises a shaft 203 fixedly connected between the two channel fixing plates 120. The slider 204 is slidably connected to the shaft 203. The push-pull rod 205 passes through the channel fixing plate 120 and extends backwardly.

Figure 7:
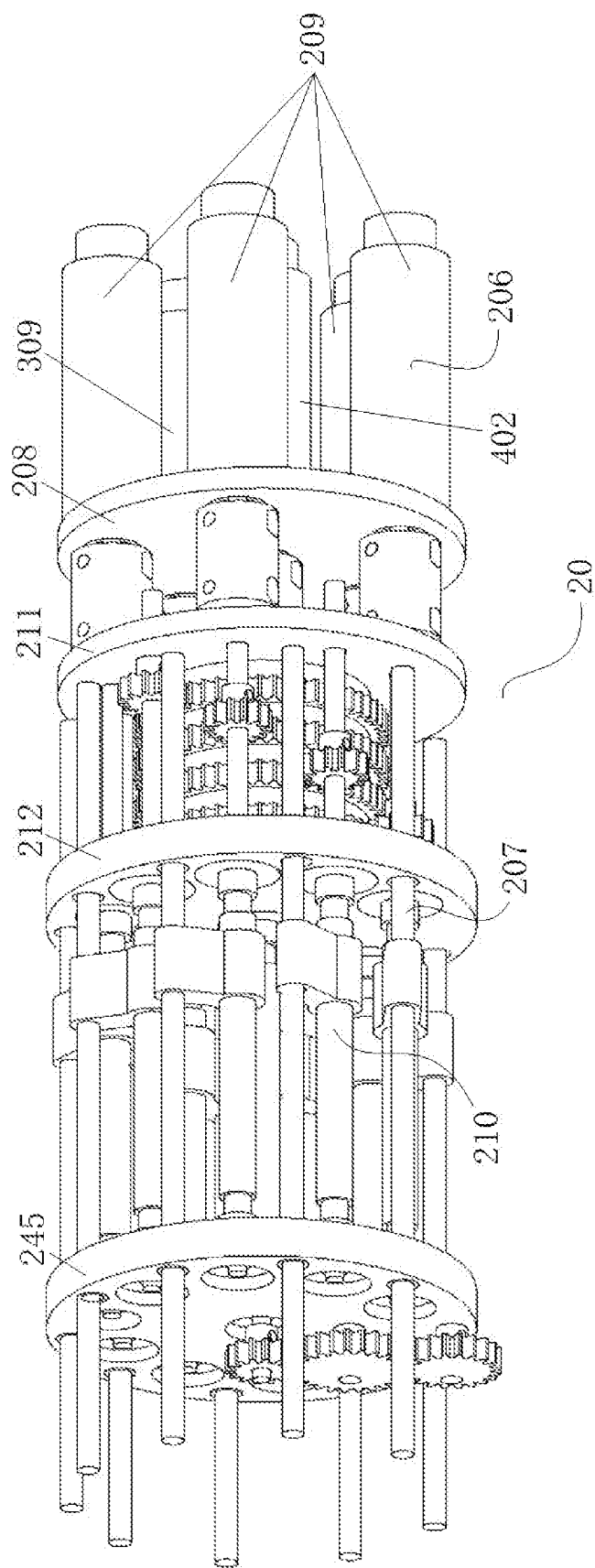
FIG. 7 is a structural schematic diagram of a motor part and a motion conversion part of a driving unit according to the present invention.
Figure 8:
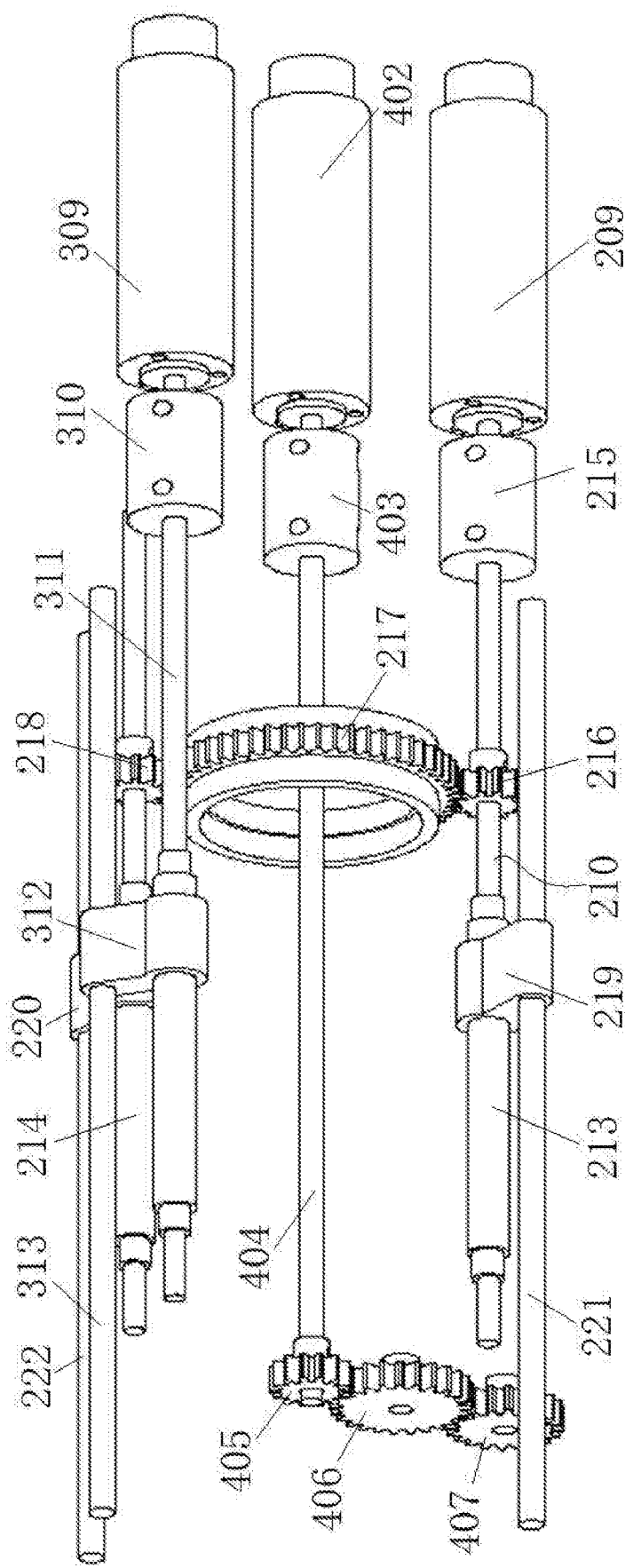
FIG. 8 is a structural schematic diagram of a transmission chain according to the present invention.

As shown in FIGS. 7 and 8, the driving unit 20 further comprises a motor part 206 and a motion conversion part 207, wherein the motor part 206 comprises a first fixing plate 208 and a plurality of (four in this embodiment) motors 209, which are securely connected to the first fixing plate 208 and are used for supplying a driving force to the driving backbone 202. In this embodiment, the motion conversion part 207 comprises a plurality of (four in this embodiment) transmission chains 210, each of the transmission chains 210 converts a rotary output of one motor 209 into a linear motion of two output rods 221, 222, and the linear motion of the two output rods 221, 222 is ultimately transferred to two push-pull rods 205 accordingly, thus driving a pair of driving backbones 202 to complete cooperative pushing and pulling movement.

As shown in FIGS. 7 and 8, the motion conversion part 207 further comprises a second fixing plate 211, a third fixing plate 212 and a fourth fixing plate 245 which are provided in front of the first fixing plate 208. Each of the transmission chains 210 comprises a first threaded rod 213 and a second threaded rod 214 which are spaced apart and rotatably supported between the third fixing plate 212 and the fourth fixing plate 245, wherein one end of the first threaded rod 213 passes through the third fixing plate 212 and the second fixing plate 211 in succession and is connected to an output shaft of the motor 209 via a coupling 215. A first gear 216 is securely connected to the first threaded rod 213 between the second fixing plate 211 and the third fixing plate 212; and the first gear 216 is in transmission connection with a second gear 218 via an idle gear 217, the second gear 218 is securely connected to the second threaded rod 214, and one end of the second threaded rod 214 passes through the third fixing plate 212. The screw direction of the first threaded rod 213 shall be different from that of the second threaded rod 214, for example, the first threaded rod 213 and the second threaded rod 214 are respectively a left-handed threaded rod and a right-handed threaded rod, and preferably, the screw pitch of the first threaded rod 213 is the same as that of the second threaded rod 214. A first nut 219 and a second nut 220 are respectively connected, in a matching manner, to the first threaded rod 213 and the second threaded rod 214 between the third fixing plate 212 and the fourth fixing plate 245, the first nut 219 is securely connected to the output rod 221, and the second nut 220 is securely connected to the output rod 222. The output rod 221 and the output rod 222 pass through the fourth fixing plate 245 to serve as an output end of the transmission chain 210.

Figure 9:
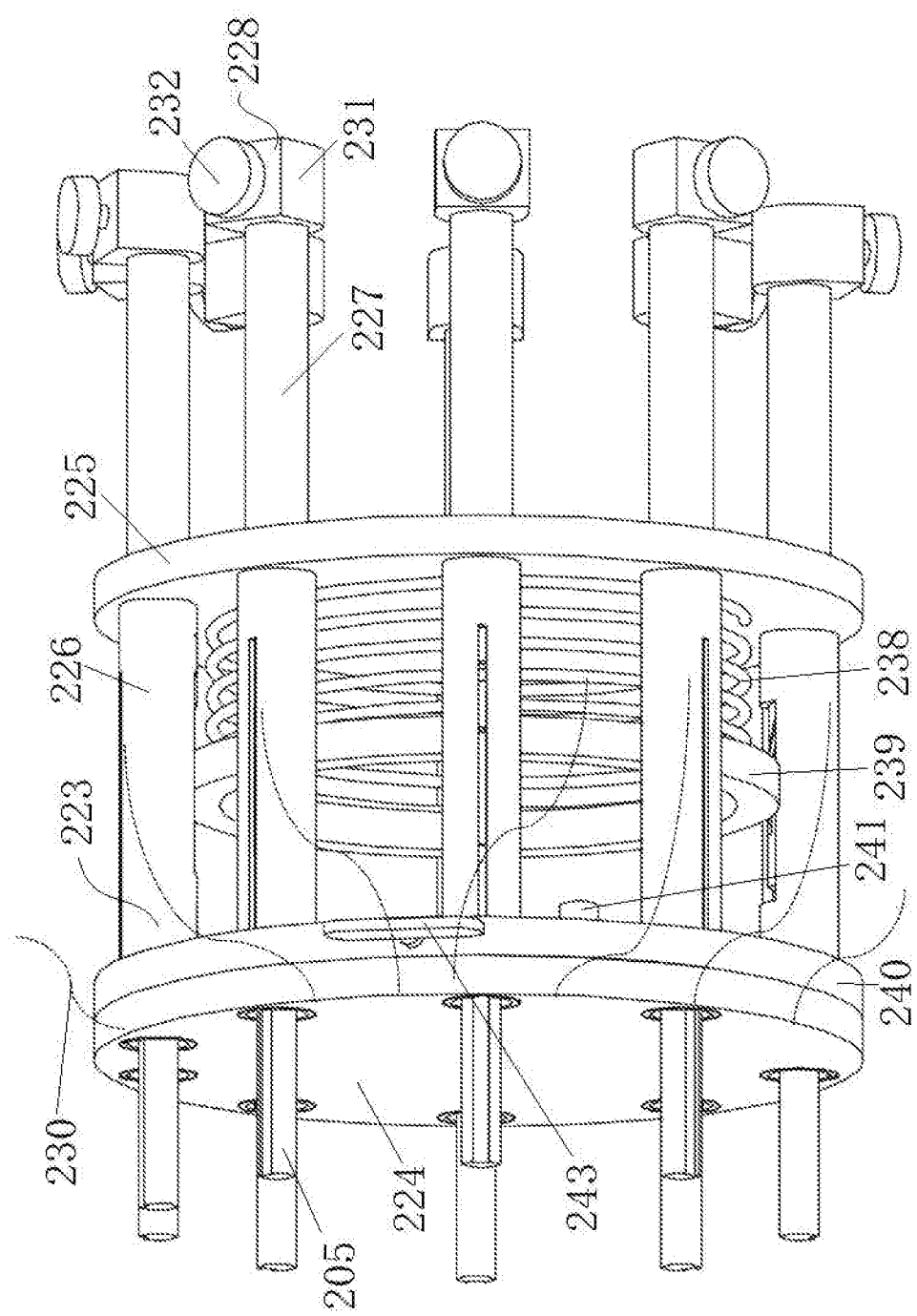
FIG. 9 is a structural schematic diagram of a sterile barrier according to the present invention.
Figure 10:
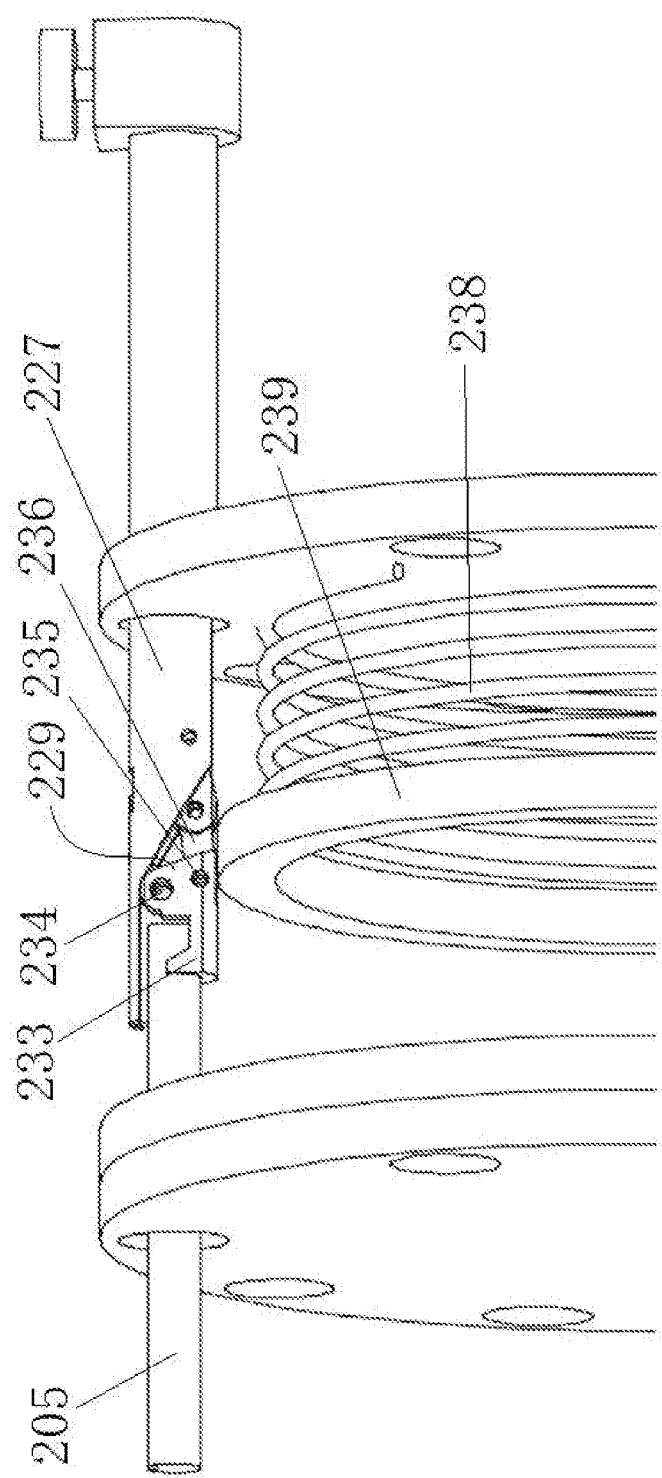
FIG. 10 is a structural schematic diagram of the sterile barrier according to the present invention when a sleeve is hidden and a base guide rod is locked with a push-pull rod.

As shown in FIGS. 1 and 9, the linear motion mechanism 201 and the motion conversion part 207 of the driving unit 20 are connected by a sterile barrier 223. The sterile barrier 223 comprises a first isolation plate 224, a second isolation plate 225, a plurality of sleeves 226 fixedly connected between the first isolation plate 224 and the second isolation plate 225, and base guide rods 227 with the number of same matching the sleeves 226. One end of each of the base guide rods 227 is connected to the output rod 221 or output rod 222 of the transmission chain 210 via a locking mechanism 228, and the other end extends into the sleeve 226 and is connected to push-pull rod 205 via a quick-locking mechanism 229. A sterile membrane 230 is securely connected to the first isolation plate 224 on the side close to the linear motion mechanism 201, and is used for isolating a sterilizable part (such as the flexible surgical instrument 10 and the linear motion mechanism 201 which are located in front of the sterile barrier 223) from an unsterilized part (such as the motion conversion part 207, the motor part 206 and a linear module 50 which are located behind the sterile barrier 223), thereby ensuring the practicability of clinical surgery.

In the above embodiment, as shown in FIG. 9, the locking mechanism 228 comprises a locking head 231 securely connected to the base guide rod 227, and a locking screw 232 connected to the locking head 231 via a screw, and when the output rod 221 or 222 is inserted into the locking head 231 of the base guide rod 227, by means of rotating the locking screw 232, the output rod 221 or 222 can tightly abut against the locking head 231, thereby realizing the connection between the base guide rod 227 and the output rod 221 or the output rod 222.

Figure 11:
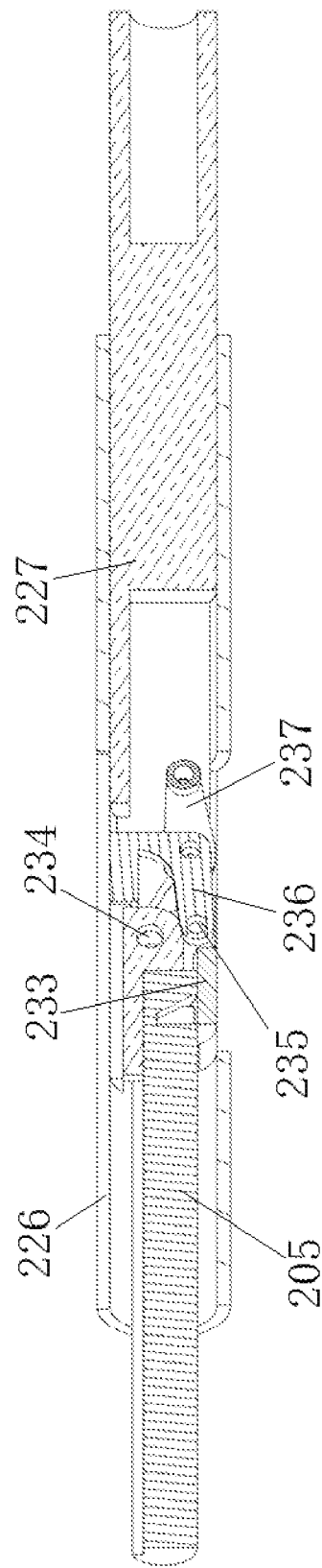
FIG. 11 is a cutaway schematic diagram of the base guide rod and the push-pull rod when they are locked according to the present invention.
Figure 12:
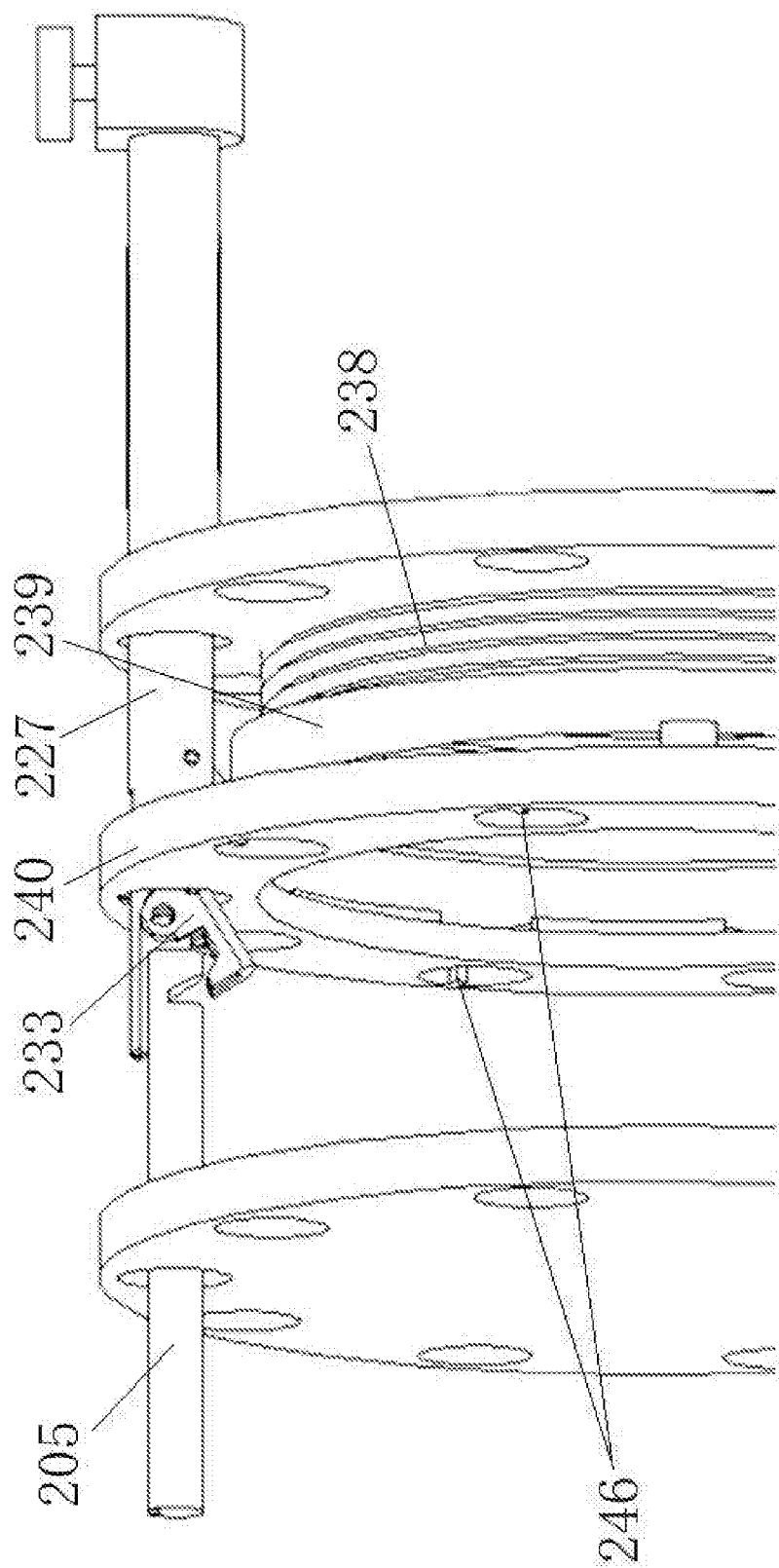
FIG. 12 is a structural schematic diagram of the sterile barrier according to the present invention when the sleeve is hidden and the base guide rod is unlocked from the push-pull rod.
Figure 13:
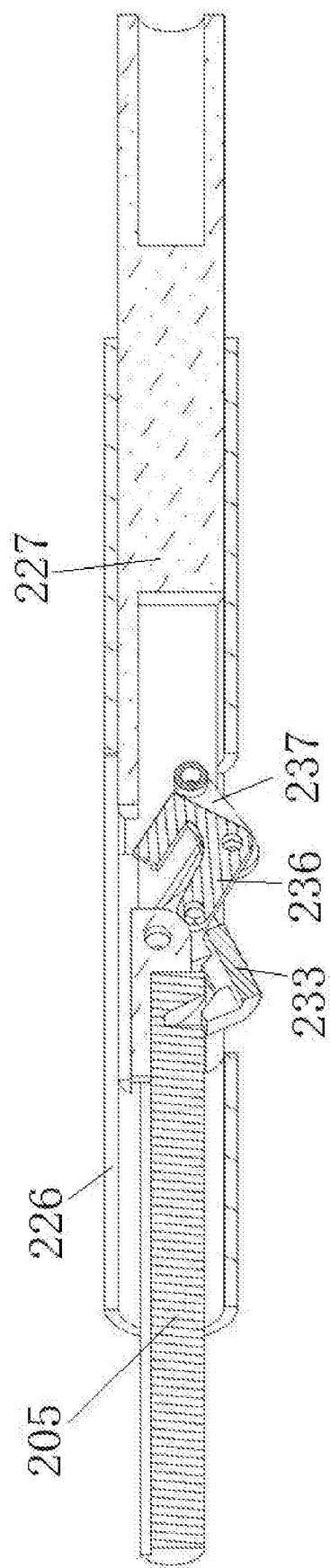
FIG. 13 is a cutaway schematic diagram of the base guide rod and the push-pull rod when separated from each other according to the present invention.

In the above embodiment, as shown in FIGS. 10-13, the quick-locking mechanism 229 comprises an engagement block 233; an engagement groove, the shape of which matches the engagement block 233, is provided at the rear end of the push-pull rod 205; and two articulation points 234, 235 are provided at the rear part of the engagement block 233, with one of the articulation points 234 being articulated with the base guide rod 227, the other articulation point 235 being connected to one end of a rocking bar 237 via a connecting rod 236, and the other end of the rocking bar 237 being articulated with the base guide rod 227. When the connecting rod 236 and the rocking bar 237 rotate, the engagement block 233 can tightly engage with or release from the push-pull rod 205, thereby realizing rapid connection or disconnection. The sleeve 226 is provided with a first groove for the engagement block 233, the connecting rod 236 and the rocking bar 237 to rotate; and the front side of the second isolation plate 225 is connected with a return spring 238, and a return baffle ring 239 is securely connected to the front end of the return spring 238. When the return spring 238 is in a loosened state, the return baffle ring 239 is attached to the first groove of the respective sleeve 226 and abuts against a connecting point of the connecting rod 236 and the rocking bar 237, and at this time the engagement block 233 engages with the push-pull rod 205. The rear side of the first isolation plate 224 is provided with a switch baffle ring 240 which is slidably connected to the respective sleeve 226, the switch baffle ring 240 is sheathed over the respective sleeves 226 via through holes, a protrusion feature 246 is provided in the respective through hole of the switch baffle ring 240, a second groove is provided on the side of the sleeve 226 opposite to the first groove, the connecting rod 236 is U-shaped (as shown in FIG. 11) with one end being close to the second groove, and when the switch baffle ring 240 moves backward, the protrusion feature 246 slides along the second groove and touches the connecting rod 236, enabling the connecting rod 236 to rotate, releasing a dead point state of the connecting rod 236 and the rocking bar 237, and making the engagement block 233 open. The rear side of the switch baffle ring 240 is provided with an ejector block 241 for pushing the return baffle ring 239. When the switch baffle ring 240 pushes the return baffle ring 239 to move backwardly, the return baffle ring 239 avoids the first groove on the sleeve 226 and does not limit the connecting rod 236 and the rocking bar 237 any longer, and at this time, the connecting point of the connecting rod 236 and the rocking bar 237 changes to outside the first groove on the sleeve 226, the engagement block 223 will release the push-pull rod 205, and the return spring 238 is in a compressed state; and when a pushing force on the switch baffle ring 240 is removed, the return baffle ring 239 returns to an original position under the action of the return spring 238.

In the above embodiment, the sterile barrier 223 further comprises a housing 242, the first isolation plate 224 and the second isolation plate 225 are both securely connected to the housing 242, a handle 243 is securely connected to an outer side of the switch baffle ring 240, a sliding groove 244 (as shown in FIG. 1) extending forward and backward is provided on the housing 242, and the handle 243 is slidably provided in the sliding groove 244. An operator can move the switch baffle ring 240 by means of the handle 243, thereby realizing the connection or disconnection between the base guide rod 227 and the push-pull rod 205.

In the above embodiment, a surgical end effector 30 (as shown in FIGS. 1 and 2) is provided in the front end of the distal structural body 101, a actuation wire 301 of the surgical end effector 30 passes through the distal structural body 101, the other end is connected to a surgical end effector driving mechanism 302 (as shown in FIG. 6) on the channel fixing plate 120, and the surgical end effector driving mechanism 302 controls the surgical end effector 30 (such as surgical forceps) by physically pushing and pulling the actuation wire 301. The actuation wire 301 may also transfer various forms of energy, such as electrical energy and high-frequency vibrations, to achieve specific surgical functions of the surgical end effector 30. The surgical end effector driving mechanism 302 comprises a base 303 securely connected to the channel fixing plate 120, a connecting rod 304 is rotatably provided on the base 303, one end of the connecting rod 304 is connected with a first slider 305, the first slider 305 is fixedly connected to a push-pull rod 306, and the rear end of the push-pull rod 306 passes through the channel fixing plate 120 and extends backwardly. The other end of the connecting rod 305 is connected with a second slider 307, the second slider 307 is slidably connected into a sliding groove 308 which is securely connected in the center of the channel fixing plate 120, and the second slider 307 is securely connected to the actuation wire 301. Accordingly, a motor 309 (as shown in FIG. 8) for supplying a driving force to the push-pull rod 306 is securely connected to the first fixing plate 208 of the motor part, an output shaft of the motor 309 is connected to one end of a third threaded rod 311 via a coupling 310, the other end of the third threaded rod 311 is rotatably supported on the fourth fixing plate 245, a third nut 312 is connected, in a matching manner, to the third threaded rod 311 between the third fixing plate 212 and the fourth fixing plate 245, and the third nut 312 is fixedly connected to an output rod 313. The output rod 313 and the push-pull rod 306 also use the base guide rod 227 on the sterile barrier 223 to transfer push-pull driving.

Figure 14:
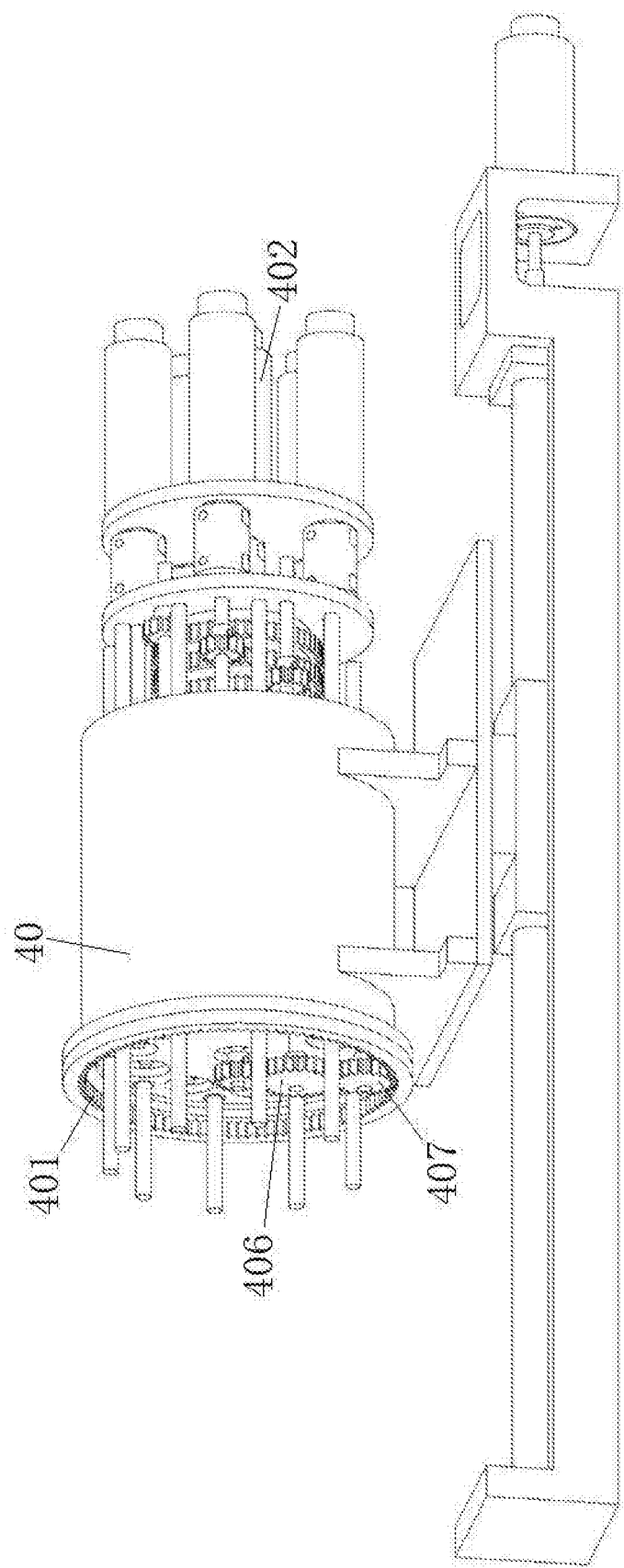
FIG. 14 is a structural schematic diagram of a part of the driving unit and a linear module according to the present invention.

In the above embodiment, as shown in FIGS. 1, 8 and 14, the present invention further comprises a shell 40. The first fixing plate 208, the second fixing plate 211, the third fixing plate 212 and the fourth fixing plate 245 are all rotatably connected to the shell 40, an inner wall of the shell 40 is securely connected to an inner ring gear 401, the first fixing plate 208 is securely connected to a motor 402, an output shaft of the motor 402 is connected to a shaft 404 via a coupling 403, the front end of the shaft 404 is securely connected to a gear 405, and the gear 405 is in transmission connection with a gear 407, which meshes with the inner ring gear 401, via an idle gear 406. When the output shaft of the motor 402 rotates, the gear 405 is driven to rotate via the shaft 404, the gear 405 drives the gear 407 to rotate via the idle gear 406, and the gear 407 will travel along the inner ring gear 401, thereby driving all the structures except the shell 40 and the inner ring gear 401 to rotate around the axis of the inner ring gear 401, realizing the overall rotation of the flexible surgical instrument 10, and achieving control over the roll angle of the distal structural body 101 and the surgical end effector 30.

In the above embodiment, as shown in FIG. 1, the present invention further comprises a linear module 50 (the linear module 50 being also separated from the sterilized part by the sterile membrane 230), which comprises a support body 501 with a sliding groove, a lead screw 502 is rotatably provided on the support body 501, the lead screw 502 is sheathed with a slider 503 which is threadedly fitted with the lead screw 502 and is slidably provided in the sliding groove, one end of the support body 501 is provided with a motor 504, and an output shaft of the motor 504 is securely connected to the lead screw 502 via a coupling. The shell 40 is securely connected to the slider 503. When the output shaft of the motor 504 rotates, the slider 503 drives the shell 40 to perform a linear motion along the sliding groove, thereby realizing a feed motion of the flexible surgical instrument 10.

Figure 15:
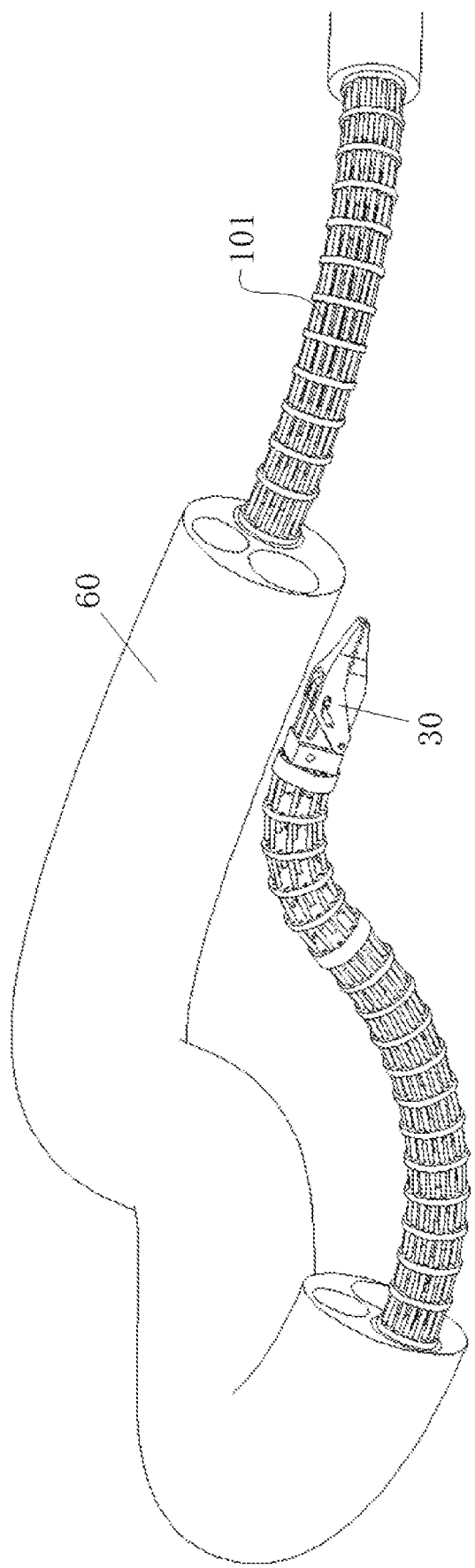
FIG. 15 is a structural schematic diagram of the distal structural body when using a flexible sheath according to the present invention.

In the above embodiment, as shown in FIG. 1, an envelope 122 is provided over the outside of the distal structural body 101 and functions to improve the smoothness of the distal structural body 101 entering a natural orifice or a surgical incision in the human body. A sheath 60 (as shown in FIG. 2) may also be provided over the outside of the envelope 122. In an application, the sheath 60 is fixed at a single incision in the abdominal cavity, and the distal structural body 101, together with the envelope 122 and the surgical end effector 30, can freely pass through a through hole in the sheath 60 for the passage of the surgical instrument and access to the surgical site. As shown in FIG. 15, in another application, the sheath 60 may also be a flexible sheath that can more easily extend into various natural orifices of the human body and adaptively change shape as the shape of the orifices, one end of the flexible sheath is fixed at the entrance of the orifice, and the distal structural body 101, together with the envelope 122 and the surgical end effector 30, can freely pass through a through hole in the flexible sheath for the passage of the surgical instrument and access to the surgical site.

The present invention has been illustrated only by means of the above embodiment, and the structure, arrangement position and connection of the components can be varied. On the basis of the technical solutions of the present invention, the improvements or equivalent changes to individual components according to the principles of the present invention should not be excluded from the scope of protection of the present invention.

The invention claimed is:

1. A flexible surgical instrument system comprising a flexible surgical instrument and a driving unit; wherein the flexible surgical instrument comprises a flexible continuous body structure composed of a distal structural body, at least one proximal structural body, and a middle connecting body; wherein the distal structural body comprises at least one distal structural segment comprising a distal spacing disk, a distal fixing disk, and distal structural backbones; wherein the at least one proximal structural body comprises a proximal structural segment comprising a proximal spacing disk, a proximal fixing disk, and proximal structural backbones; wherein the middle connecting body comprises two channel fixing plates and a structural backbone guide channel provided between the two channel fixing plates; wherein the distal structural backbones are securely connected, in one-to-one correspondence, to or are the same as the proximal structural backbones, a proximal end of each of the proximal structural backbones is securely connected to the proximal fixing disk, and the proximal structural backbones passing through the proximal spacing disk, the structural backbone guide channel in sequence, and the distal structural backbones passing through the distal spacing disk, and a distal end of the distal structural backbones is securely connected to the distal fixing disk; and wherein the driving unit comprises a motor part, a motion conversion part, and a plurality of linear motion mechanisms, wherein a sterile barrier is provided between the motion conversion part and the plurality of linear motion mechanisms; and the motor part comprises a motor fixing plate and a first motor securely connected to the motor fixing plate, the motion conversion part comprises a plurality of first transmission chains, each of the first transmission chains converts a rotary output of the first motor into a linear motion of two first output rods, the linear motion of each of the two first output rods is transferred to an input end of each of the linear motion mechanisms through the sterile barrier, an output end of each of the linear motion mechanisms is securely connected to one end of one driving backbone passing through the proximal spacing disk, and the other end of the one driving backbone is securely connected to the proximal fixing disk.

2. The flexible surgical instrument system of claim 1, wherein each of the plurality of linear motion mechanisms comprises a shaft securely connected between the two channel fixing plates and a slider slidably connected to the shaft, the slider serves as the output end of each of the linear motion mechanism and is securely connected to the one driving backbone, the slider is also securely connected to one end of a first push-pull rod, and the first push-pull rod passes through the two channel fixing plates and another end of the first push-pull rod is connected to one of the two first output rods through the sterile barrier.

3. The flexible surgical instrument system of claim 1, wherein the motion conversion part further comprises a first motion conversion fixing plate, a second motion conversion fixing plate, and a third motion conversion fixing plate which are provided in front of the motor fixing plate; each first transmission chain of the plurality of first transmission chains comprises a first threaded rod and a second threaded rod which are spaced apart and rotatably supported between the second motion conversion fixing plate and the third motion conversion fixing plate, and a rear end of the first threaded rod passes through the second motion conversion fixing plate and the first motion conversion fixing plate in sequence and is connected to an output shaft of the first motor via a coupling; a first gear is securely connected to the first threaded rod between the first motion conversion fixing plate and the second motion conversion fixing plate, the first gear is in transmission connection with a second gear via an idle gear, and the second gear is securely connected to the second threaded rod; a first nut and a second nut are respectively connected, in a matching manner, to the first threaded rod and the second threaded rod between the second motion conversion fixing plate and the third motion conversion fixing plate; and the two first output rods are respectively securely connected to the first nut and the second nut, and front ends of the two first output rods pass through the third motion conversion fixing plate.

4. The flexible surgical instrument system of claim 3, wherein a screw direction of the first threaded rod is different from that of the second threaded rod, and a screw pitch of the first threaded rod is the same as that of the second threaded rod.

5. The flexible surgical instrument system of claim 1, wherein the sterile barrier comprises a first isolation plate, a second isolation plate, a plurality of sleeves securely connected between the first isolation plate and the second isolation plate, and base guide rods having the same number as the plurality of sleeves; wherein one end of each of the base guide rods is connected to a front end of one of the two first output rods via a locking mechanism, and another end of each of the base guide rods extends into each of the plurality of sleeves and is connected to a rear end of one first push-pull rod via a quick-locking mechanism; and a sterile membrane for isolating a sterilizable part from an unsterilized part of the flexible surgical instrument system is securely connected to the first isolation plate, and
    the locking mechanism comprising:
        a locking head with a threaded through hole that is securely connected to each of the base guide rods; and
        a locking screw is connected, in a matching manner, into the threaded through hole, and when screwed into the threaded through hole, the locking screw tightly abuts against each of the two first output rods, and
    the quick-locking mechanism comprising:
        an engagement block;
        an engagement groove matching the engagement block is provided at the rear end of the one first push-pull rod; and
        two articulation points are provided at a rear part of the engagement block, with one of the articulation points being articulated with one of the base guide rods, an other articulation point being connected to one end of a rocking bar via a connecting rod, and an other end of the rocking bar being articulated with one of the base guide rods.

6. The flexible surgical instrument system of claim 5, wherein each sleeve of the plurality of sleeves is provided with a first groove for rotation of the engagement block, the connecting rod and the rocking bar; and a front side of the second isolation plate is connected with a return spring, and a return baffle ring is securely connected to a front end of the return spring; wherein when the return spring is in a loosened state, the return baffle ring is attached to the first groove of each sleeve of the plurality of sleeves and abuts against a connecting point of the connecting rod and the rocking bar.

7. The flexible surgical instrument system of claim 6, wherein a rear side of the first isolation plate is provided with a switch baffle ring which is slidably connected to a respective sleeve of the plurality of sleeves, the switch baffle ring is sheathed over the respective sleeve of the plurality of sleeves via through holes, a protrusion feature is provided in a respective through hole of the through holes of the switch baffle ring, a second groove is provided on a side of the respective sleeve of the plurality of sleeves opposite to the first groove, and the connecting rod is a U-shaped connecting rod with one end being close to the second groove; and when the switch baffle ring moves backwardly along the respective sleeve of the plurality of sleeves, each protrusion feature of each respective through hole slides along the second groove and touches the end of the U-shaped connecting rod, enabling the U-shaped connecting rod to rotate.

8. The flexible surgical instrument system of claim 1, wherein a surgical end effector is provided in a front end of the distal structural body, an actuation wire of the surgical end effector passes through the distal structural body, one end of the actuation wire is connected to a surgical end effector driving mechanism on the two channel fixing plates, the surgical end effector driving mechanism comprises a base securely connected to one of the two channel fixing plates, a connecting rod is rotatably provided on the base, one end of the connecting rod is connected with a first slider which is securely connected to a second push-pull rod, and a rear end of the second push-pull rod passes through the two channel fixing plates and extends backwardly; an other end of the connecting rod is connected with a second slider which is slidably connected into a sliding groove securely connected to one of the two channel fixing plates, and the second slider is securely connected to the actuation wire; and
    a second motor is securely connected to the motor fixing plate, and the motion conversion part further comprises a second transmission chain which converts a rotary output of the second motor into a linear motion of a second output rod; and the linear motion of the second output rod is transferred to the second push-pull rod via the sterile barrier.

9. The flexible surgical instrument system of claim 8, wherein the motion conversion part further comprises a first motion conversion fixing plate, a second motion conversion fixing plate and a third motion conversion fixing plate which are provided in front of the motor fixing plate; and the second transmission chain comprises a threaded rod, a rear end of the threaded rod is connected to the second motor via a coupling between the motor fixing plate and the first motion conversion fixing plate, both the second motion conversion fixing plate and the third motion conversion fixing plate rotatably support the threaded rod, a nut is connected, in a matching manner, to the threaded rod between the second motion conversion fixing plate and the third motion conversion fixing plate, and the nut is securely connected to the second output rod.

10. The flexible surgical instrument system of claim 1, wherein the flexible surgical instrument system further comprises a shell, the motor fixing plate is rotatably connected to the shell, and an inner ring gear is securely connected to an inner wall of the shell; and a second motor is securely connected to the motor fixing plate, an output shaft of the second motor is connected to a shaft via a coupling, and a front end of the shaft is securely connected to a gear in transmission connection with another gear via an idle gear, the another gear meshing with the inner ring gear.

11. The flexible surgical instrument system of claim 1, wherein the flexible surgical instrument system further comprises a shell and a linear module, the linear module comprises a support body, a second motor securely connected to the support body, and a linear feed mechanism securely connected to an output shaft of the second motor, wherein an output end of the linear feed mechanism is securely connected to the shell, and the second motor drives the shell by means of the linear feed mechanism, to drive the driving unit, the sterile barrier and the flexible surgical instrument to perform a linear motion.

12. The flexible surgical instrument system of claim 11, wherein the linear feed mechanism comprises a lead screw rotatably connected to the support body, the lead screw is sheathed with a slider which is threadedly fitted with the lead screw, a linear sliding groove is provided on the support body, and the slider is slidably provided in the linear sliding groove; and the output shaft of the second motor is securely connected to the lead screw via a coupling.

13. The flexible surgical instrument system of claim 1, wherein a number of the at least one proximal structural body is equal to a number of the distal structural segments.

\* \* \* \* \*